US008311183B2

(12) United States Patent  (10) Patent No.: US 8,311,183 B2
O'Dwyer et al.  (45) Date of Patent: Nov. 13, 2012

(54) ONLINE ENERGY DISPERSIVE X-RAY DIFFRACTION ANALYSER

(75) Inventors: Joel O'Dwyer, Shellharbour (AU); James Tickner, Meadows (AU)

(73) Assignee: Commonwealth Scientific and Industrial Research Organisation, Australian Capital Territory (AU)

(*) Notice: Subject to any disclaimer, the term of this patent is extended or adjusted under 35 U.S.C. 154(b) by 157 days.

(21) Appl. No.: 12/681,373

(22) PCT Filed: Oct. 3, 2008

(86) PCT No.: PCT/AU2008/001456
§ 371 (c)(1),
(2), (4) Date: Aug. 4, 2010

(87) PCT Pub. No.: WO2009/043095
PCT Pub. Date: Apr. 9, 2009

(65) Prior Publication Data
US 2010/0303206 A1    Dec. 2, 2010

(30) Foreign Application Priority Data
Oct. 3, 2007 (AU) .............................. 2007905416

(51) Int. Cl.
*G01N 23/20* (2006.01)
(52) U.S. Cl. .......................................... 378/71; 378/70
(58) Field of Classification Search ............. 378/70–71, 378/72, 80, 82, 83, 84, 85, 57
See application file for complete search history.

(56) References Cited

U.S. PATENT DOCUMENTS
5,008,911 A    4/1991    Harding
(Continued)

FOREIGN PATENT DOCUMENTS
WO    2005/055827    6/2005

OTHER PUBLICATIONS
Notice of the First Office Action in CN 200880115317.2 dated Aug. 17, 2011.
(Continued)

*Primary Examiner* — Hoon Song
(74) *Attorney, Agent, or Firm* — Nixon & Vanderhye PC

(57) ABSTRACT

An on-line EDXRD analyser including (i) a housing defining an analysis zone and having a passageway through it to allow transport of material in a process stream to pass through the analysis zone, (ii) a collimated source of polychromatic X-rays, (iii) an energy-resolving (ER)X-ray detector, (iv) a primary beam collimator disposed between the source of X-rays and the (ER)X-ray detector comprising an annular slit which defines an incident beam of polychromatic X-rays to irradiate a portion of the analysis zone, (v) a scatter collimator disposed between the primary beam collimator and the ERX-ray detector, the scatter collimator comprising an annular slit which defines a diffracted beam of X-rays scattered by the material to converge towards the ERX-ray detector, and (vi) a detector collimator comprising a conical opening which further defines the diffracted beam of X-rays scattered by the material. The ERX-ray detector measures an energy spectrum of the diffracted X-rays at a predetermined diffraction angle defined by the relative positioning of (ii) to (vi), and where one of (iv) and (v) comprises an aperture arranged to enable a detector to measure the transmission of a direct beam of X-rays through the material.

19 Claims, 10 Drawing Sheets

U.S. PATENT DOCUMENTS

| | | |
|---|---|---|
| 5,231,652 A | 7/1993 | Harding |
| 5,394,453 A | 2/1995 | Harding |
| 5,510,644 A | 4/1996 | Harris et al. |
| 6,118,850 A | 9/2000 | Mayo et al. |
| 2005/0104603 A1* | 5/2005 | Peschmann et al. .......... 324/637 |

OTHER PUBLICATIONS

Sutherland, D.N. and Gottlieb P., "Application of Automated Quantitative Mineralogy in Mineral Processing," Miner. Eng., 4, pp. 753-762.

Roach, G., 1998, "Application of Emerging Analytical Technologies to the Bayer Process, technology—Australia's Future: new Technology for Traditional Industries," Proceedings of the 1998 Invitational Symposium, Fremantle, Australia.

Smallbone, Allan H., "Automated On-Line Analysis for Controlling Industrial Processes," Pure Appl. Chem., vol. 49, 1977, pp. 1609-1620.

Lim, C.S., and Sowerby, B.D., "On-line Bulk Elemental Analysis in the Resource Industries Using Neutron-Gamma Techniques," Journal of Radioanalytical and Nuclear Chemistry, vol. 264, No. 1 (2005) pp. 15-19.

Scarlett, Nicola V.Y., Madsen, Ian C., Manias, Con, Retallack, David, "On-line X-ray diffraction for quantitative phase analysis: Application in the Portland cement industry," Powder Diffraction, 16(2), Jun. 2001, pp. 71-80.

Farquharson, M.J. and Speller, R.D., Trabecular Bone Mineral Density Measurements Using Energy Dispersive X-Ray Diffraction (EDXRD), Radiat. Phys. Chem., vol. 51, No. 4-6, (1998), pp. 607-608.

* cited by examiner

ONLINE ENERGY DISPERSIVE X-RAY DIFFRACTION ANALYSER

CROSS-REFERENCE TO RELATED APPLICATIONS

This application is a national stage application of and claims the benefit of PCT Application No. PCT/AU2008/001456, filed on Oct. 3, 2008, and published as WO 2009/043095, which claims priority to Australian Provisional Patent Application No 2007905416 filed on Oct. 3, 2007 The disclosure of the prior applications is considered part of (and is incorporated by reference in) the disclosure of this application.

TECHNICAL FIELD

The present invention relates generally to an on-line energy dispersive X-ray diffraction analyser for mineralogical analysis of material in a process stream. The invention is particularly targeted towards mineralogical analysis of mineral slurries and dry powders.

BACKGROUND ART

Many mineral processing plants and techniques for metal production are sensitive to the mineralogical content as well as the elemental composition of the feedstock fed into the processing plant. In many cases, the mineralogical composition rather than the chemical composition of a process stream is the most important factor in terms of plant performance in mineral processing.

Direct mineralogical analysis of process streams is mainly limited to off-line techniques. Widely used techniques include scanning electron microscopy [Sutherland 1991][1] and conventional X-ray diffraction (XRD) [Roach 1998][2]. These techniques require removal of a small sample, or assay, from the process stream which is taken to a laboratory for analysis. However, the small quantity of sample normally extracted for such assays, from the immense volumes usually encountered in a processing plant, is generally not well related to the information needed for accurate control which leads to large sampling errors. In addition, the lag time before the analysis is available can result in substantial cost. Subsequently, off-line analysis is considered ill suited to process control, especially for slurries, which demands regular and rapid analysis of the process stream.

Conventional XRD is based on angle-dispersive techniques which tend to require expensive equipment. An alternative technique is the energy dispersive technique EDXRD which is based on polychromatic radiation. The interference of the lattice planes reflections corresponding to the Bragg-equation is investigated by the diffraction intensity of the different wavelengths rather than varying the Bragg-angle as in conventional XRD.

On-line monitoring of process streams, on the other hand, is primarily restricted to elemental analysers, which measure the chemical composition of the material in the process stream. Widely used on-line elemental analysis techniques for process monitoring and control include X-ray fluorescence (XRF) [Smallbone 1977][3] and prompt neutron/gamma-ray activation analysis (PGNAA) [Sowerby 2005][4]. The mineralogical content of the stream is determined using prior knowledge of the relationship between the chemical and mineralogical composition of the material in question. However such techniques are unable to distinguish between minerals (for example anatase and rutile) having the same chemical composition (in this case $TiO_2$). Furthermore the presence of the same element in a number of different materials making up a process stream can result in misleading results. For example if the quantity of quartz ($SiO_2$) needs to be known, the results will be affected by the presence of Si and O in other materials contained in the process stream.

A quasi on-line mineralogical analyser using conventional angular dispersive X-ray diffraction has been proposed [Scarlett 2001][5]. However this technique requires complex automated sample handling equipment and has had only limited application.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

The present invention is an on-line energy dispersive X-ray diffraction (EDXRD) analyser for mineralogical analysis of material in a process stream, the EDXRD analyser comprising:

a housing defining an analysis zone and having a passageway through it to allow transport of material in a process stream to pass through the analysis zone;

a collimated source of polychromatic X-rays and an energy resolving X-ray detector, each of which are disposed in relation to the housing;

a primary beam collimator disposed between the collimated source of polychromatic X-rays and the energy resolving X-ray detector, the primary beam collimator comprising an annular slit which defines an incident beam of polychromatic X-rays to irradiate a portion of the analysis zone;

a scatter collimator disposed between the primary beam collimator and the energy resolving X-ray detector, the scatter collimator comprising an annular slit which defines a diffracted beam of X-rays scattered by the material to converge towards the energy resolving X-ray detector; and a detector collimator comprising a conical opening which further defines the diffracted beam of X-rays scattered by the material;

where the energy resolving X-ray detector measures an energy spectrum of the diffracted X-rays at a predetermined diffraction angle, where the relative positioning of each of the source of polychromatic X-rays, the primary beam collimator, the scatter collimator, the energy resolving X-ray detector and detector collimator defines the diffraction angle, and where at least one of the primary beam collimator and the scatter collimator further comprises an aperture, the or each aperture arranged to enable a detector to measure the transmission of a direct beam of X-rays through the material.

In one embodiment the primary beam collimator and the scatter collimator each have an aperture, the respective apertures aligned with each other along a central axis between the source of X-rays and the energy resolving X-ray detector to enable the energy resolving detector to measure the transmission of a direct beam of X-rays through the material.

In an optional embodiment a second detector separate from the energy resolving detector measures the transmission of a direct beam of X-rays through the material. In such an embodiment the scatter collimator includes an aperture aligned with respect to a segment of the annular slit of the primary beam collimator to enable the second detector to measure the transmission of a direct beam of X-rays through the material.

The EDXRD analyser may further comprise a signal processor to process signals from the detector(s) so as to determine planar spacings of minerals within the process stream. The signal processor may be operable to determine planar spacings and/or the proportions of different mineral species present in the material. The processor may divide the measured energy spectrum of the diffracted X-rays by the measured transmission of the direct beam of X-rays through the material to account for attenuation losses.

Preferably the annular slits of the respective primary beam collimator and scatter collimator are conical in shape. The annular slits of the respective primary beam collimator and scatter collimator are preferably circularly symmetric about a central axis between the source of X-rays and the energy resolving X-ray detector. The width of the annular slits of the respective primary beam collimator and scatter collimator may be within the range of a tenth of a millimeter to several millimeters.

In a preferred embodiment the annular slits of the respective primary beam collimator and scatter collimator are discontinuous. Preferably the discontinuity will be the smallest possible fraction of the total circumference of the annular slit in order to support an inner conical section.

Preferably the incident beam of X-rays which irradiates the analysis zone is in the form of a surface of a divergent hollow cone. The diffracted beam of X-rays scattered by the material is preferably in the form of a surface of a convergent hollow cone. Subsequently, the energy resolving detector receives a converging conical diffracted beam which corresponds to an intersection between the divergent hollow cone and the converging hollow cone.

In one embodiment, the EDXRD analyser may further comprise a translation stage upon which is mounted the primary beam collimator and scatter collimator. Optionally, separate translation stages may be provided to separately mount the respective primary beam collimator and scatter collimator.

In one embodiment, the housing which defines the analysis zone may be a pipeline, tube, or the like through which the process stream may pass, or be propelled. The pipeline may be manufactured from a low-density, non diffracting material. Means to propel the process stream may be by way of a pump or gravity feed. It should be appreciated that in such an embodiment, the collimated source of polychromatic X-rays and the energy resolving X-ray detector will be situated on opposite sides of the pipeline.

The EDXRD analyser may further comprise a shielding enclosure for accommodating components of the analyzer and having a passageway for the pipeline to pass. The enclosure may be a radiation shielding enclosure. The radiation shielding enclosure may be lined with lead.

In a further embodiment, the housing may be a vessel, tank, or the like container having a volume. The passageway may comprise an inlet and an outlet to enable the process stream to be propelled through the volume of the vessel. The pressure of the process stream may be sufficient to effect the transfer of material through the vessel; optionally, a pump or gravity feed may be used. The EDXRD analyser may further comprise a shielding enclosure for accommodating components of the analyzer. Optionally, or in addition, the vessel may form at least a portion of the shielding enclosure. The collimated source of polychromatic X-rays and the energy resolving X-ray detector may be situated wholly within the vessel, tank, or the like container. Optionally, the collimated source of polychromatic X-rays and the energy resolving X-ray detector respectively extend through opposing walls of the vessel. Preferably, access ports are provided on opposing walls of the vessel and the source of polychromatic X-rays and the energy resolving X-ray detector are mounted to a periphery of a respective access port. Still preferably, the source of polychromatic X-rays and the energy resolving X-ray detector are sealably mounted to a periphery of a respective access port to prevent leakage of material from within the vessel. In an embodiment where the housing is a vessel, tank, container, or the like, the EDXRD analyser may comprise a first translation stage upon which the X-ray source and source collimator are mounted and a second translation stage upon which the energy resolving X-ray detector and detector collimator are mounted. In such an embodiment, the primary beam collimator and the scatter collimator are rigidly fixed relative to the housing. For instance, each of the primary beam collimator and the scatter collimator may be respectively mounted to a first end of a projection means which projects into an interior of the housing. The respective projection means may be coupled to one another in such a way to still enable the passage of material through the portion of the analysis zone.

In any of the embodiments, the, or each, translation stage may comprise one or more micrometers to enable fine adjustment of the primary beam collimator and scatter collimator in a direction normal to a central axis between the source of X-rays and the energy resolving X-ray detector.

The source of polychromatic X-rays is preferably a sealed X-ray tube. Sealed X-ray tubes contain a permanent vacuum and as a result are maintenance free. Sealed X-ray tubes are typically characterized as having a reflective target and sealed operating enclosure that has a very high level of vacuum created and sealed during manufacture. Advantages of sealed X-ray tubes are that they operate at lower kV and have long operating lifetimes.

Preferably the source of polychromatic X-rays is operated at a voltage of, or about, 150 kV. More preferably the source of X-ray is operated at voltage between 80 kV and 200 kV. Such operation produces polychromatic X-rays which have energies within the range 0 keV to 150 keV and more preferable in the range 20 keV to 200 keV. Most preferably the source produces polychromatic X-rays within the range 20 keV to 80 keV.

The energy resolving X-ray detector is preferably a CdTe detector. Optionally the detector may be another high-resolution semiconductor that can be operated at or near room temperature, for example CZT or HgI. Optionally the detector may be an HPGe detector. In an embodiment where the detector is an HPGe detector the analyser may additionally comprise a cooling system to cool the detector to a temperature sufficient to measure spectral data.

The collimated source of polychromatic X-rays may comprise a source collimator in close proximity to, or attached to the source of X-rays. The source collimator may have a cylindrical-shaped aperture, or a conical-shaped aperture, having a diameter to substantially reduce background scatter.

Any one or more of the primary beam collimator, scatter collimator and detector collimator may comprise a radiation shield. The shield may adhere to a first surface (face) of the respective collimator which is subjected to the beam of X-rays.

The housing, and/or, shielded enclosure may be made of any suitable material having a sufficiently high atomic number to substantially absorb X-rays (other than those reaching the detector, those absorbed by the material).

The collimated source of polychromatic X-rays and the energy resolving X-ray detector may be disposed entirely within the substantially shielded enclosure.

The process stream may comprise, in a non-limiting example, a mineral slurry. Optionally, the process stream may comprise a dry powder, conveyed pneumatically, by gravity, or by a screw-feeder or similar device.

BRIEF DESCRIPTION OF THE DRAWINGS

An example of the invention will now be described with reference to the accompanying drawings:

FIG. 5b is a schematic drawing of a side view of the arrangement shown in FIG. 5a;

FIG. 9b is a schematic drawing of an instrument referred to in the background art and in FIG. 9a;

BEST MODES FOR CARRYING OUT THE INVENTION

Figure 1:
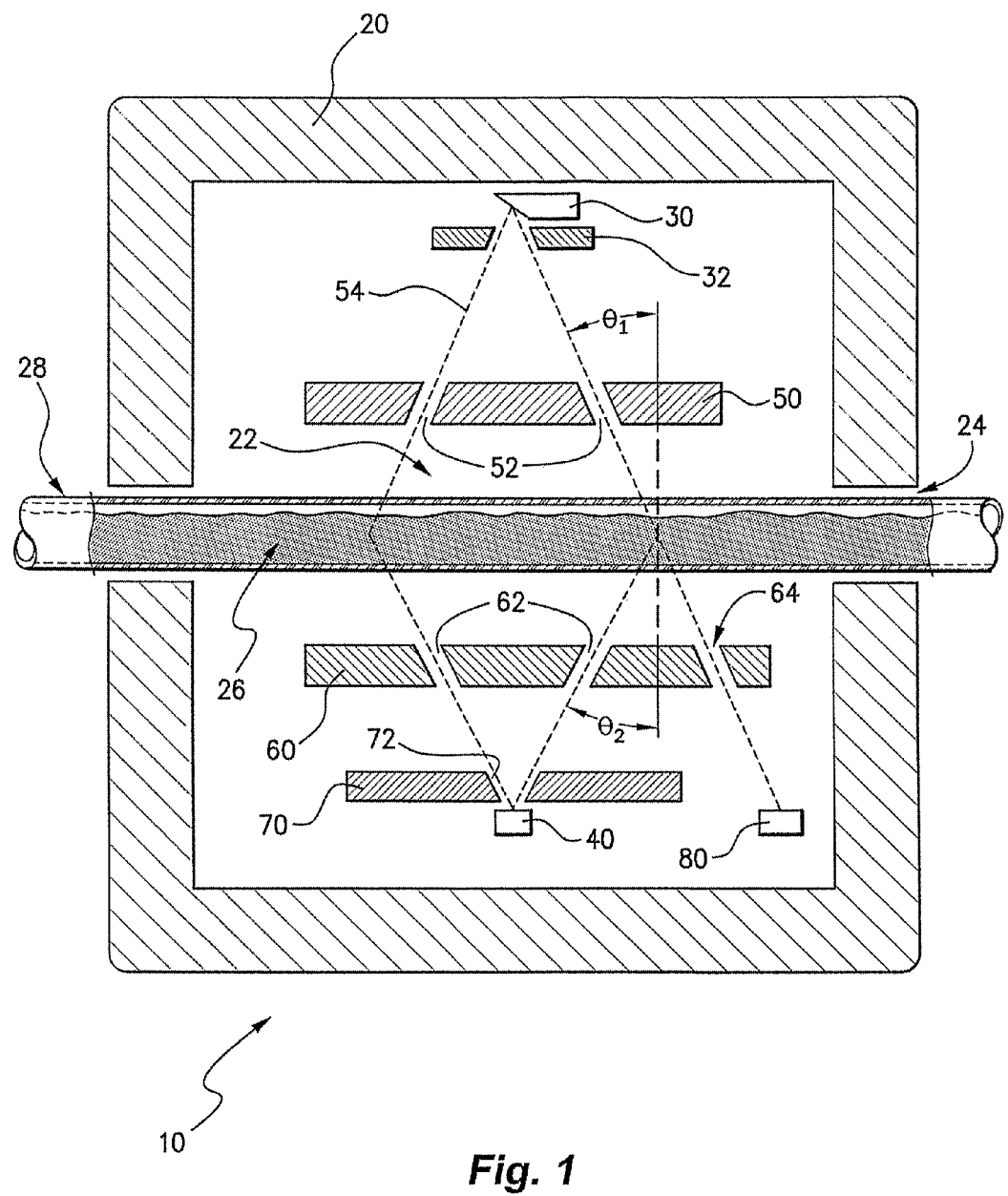
FIG. 1 is a schematic drawing of a practical arrangement of an on-line energy dispersive X-ray diffraction (EDXRD) analyser for on-line mineralogical analysis.

Referring now to the drawings in which like numerals represent like elements throughout the several views. FIG. 1 schematically illustrates a practical arrangement for installation of an on-line energy dispersive X-ray diffraction analyser 10 positioned with respect to a process stream of a pumped mineral slurry. Whilst the configuration of the apparatus in the following description is described in relation to the analysis of a pumped mineral slurry, it should be appreciated that the configuration of the apparatus is suitable for the analysis of dry powders.

The analyser 10 comprises a housing in the form of a pipeline 28 defining an analysis zone 22 and having a passageway through it to allow transport of mineral content 26 in a process stream through the analysis zone 22. The mineral content 26 is propelled through a pipeline 28 which passes through the analysis zone 22, by way of a pump (not shown). The pipeline 28 is manufactured from a low-density, non diffracting material, such as a plastic.

A radiation shielding enclosure 20 lined with lead is provided and has a passageway 24 for the pipeline 28 to pass.

A polychromatic X-ray source 30 and an energy resolving X-ray detector 40 are disposed within the shielded enclosure 20 and are situated on opposing sides of the pipeline 28. The source 30 generates a polychromatic incident X-ray beam. Any suitable X-ray tube, as is known in the art, with a suitable anode type, may be used to generate the polychromatic beam. For instance the X-rays may be produced using a Hamamatsu L8121-01 Microfocus X-ray tube, which in use is operated at a voltage of 120 kV and a current of 0.5 mA.

Attached to the source of polychromatic X-rays 30 is a source collimator 32 composed of a lead block and having a conical-shaped aperture at its centre.

The energy resolving X-ray detector 40 is an Amptek XR-100T-CdTe detector that permits very high energy resolution, of approximately 570 eV at 60 keV. The use of CdTe diodes detectors has a number of advantages over other possible detectors. Unlike high-purity germanium (HPGe) detectors, CdTe detectors do not require liquid nitrogen cooling. They are also less expensive, smaller in size and have comparable energy resolution to HPGe. CdTe detectors also provide better charge transport properties than the similar cadmium zinc telluride (CZT) detector, so a much improved spectrum is observable.

Disposed between the collimated source of polychromatic X-rays 30 and the analysis zone 22 is a primary beam collimator 50 which is formed from steel. The primary beam collimator 50 comprises an annular slit 52 there-through, of radius $r_1$ and with surfaces sloped at the angle $\theta_1$, which defines an incident beam 54 of X-rays to irradiate the analysis zone 22. The incident beam 54 is in the form of a surface of a divergent hollow cone. Within the material in the analysis zone, some coherent scattering will occur, an optimum of which for a given measurement will take place within a relatively narrow range of angles about the angle $\theta_1+\theta_2$.

A scatter collimator 60, also formed from steel, is disposed between the analysis zone 22 and the energy resolving X-ray detector 40. The scatter collimator 60 also comprises an annular slit 62 to define a diffracted beam of X-rays scattered by the material to converge towards the detector 40, the annular slit 62 having a radius $r_2$, again with inner surfaces sloped at $\theta_2$.

A detector collimator 70, formed from steel, is provided. The detector collimator 70 further defines the diffracted beam of X-rays scattered by the material. The detector collimator 70 has a centrally positioned conical-shaped aperture 72 which allows X-rays to reach the detector 40. The conical-shaped aperture 72 is formed using wire cutting. The inner surface of the conical-shaped aperture 72 is sloped such that it is parallel to the direction of travel of X-rays that pass through the scatter collimator's aperture 62 and to the energy resolving detector 40. The relative geometry of the scatter collimator's aperture 62 and the energy resolving detector 40 is such that the energy resolving X-ray detector 40 measures the energy spectrum of X-rays scattered at a narrow range of angles about the selected angle $\theta=\theta_1+\theta_2$. Subsequently, the energy resolving detector 40 receives a converging conical diffracted beam which corresponds to an intersection between the divergent hollow cone and the converging hollow cone.

The optimum diffraction angle $\theta$ will depend on the crystal structure of the sample material under investigation and the energy of the incident photons. Bragg's Law, defined below, describes the conditions under which the constructive interference of X-ray photons occurs.

$$\lambda = 2d \sin(\theta/2), \quad (1)$$

where $\lambda$, is the X-ray wavelength and d is the atomic planar spacing. In the case of EDXRD, it is more convenient to write Equation 1 in terms of the X-ray energy rather than the wavelength $$E = \frac{hc}{2d\sin(\theta/2)}, \quad (2)$$

where E is the X-ray energy, h is Planck's constant and c is the speed of light. By detecting the energy spectrum of X-rays that are scattered at a fixed angle (EDXRD), it is possible to deduce the planar spacings (d) of minerals present and therefore determine the proportions of different mineral species present in a material.

There may be many scattering planes within a given material, presenting a range of plane spacings (d). Some energies of the incident spectrum will satisfy Bragg's Law for constructive interference (for a particular value of d). This leads to the detection of a spectrum of photon energies that will have a unique 'signature' related to the material under investigation.

The scatter collimator 60 further comprises an aperture 64. A second detector 80 (also an energy resolving detector) is provided to measure the transmission of a direct beam of X-rays having passed through the slit 52 of the primary beam collimator, through the material and through the aperture 64 of the scatter collimator 60 (i.e. to measure the portion of the transmitted beam which passes through without diffraction). The second detector 80 is preferably of the same type as the energy resolving detector 40. Optionally the second detector 80 may be a lower resolution detector, such as a scintillator crystal coupled to a photodiode or photo-multiplier. The outputs from detectors 40 and 80 are coupled to processing electronics (not shown).

The main effect the thickness of the sample has on the diffraction spectrum is to determine the degree to which low-energy X-rays are absorbed in the material. Since low-energy X-rays are less likely to penetrate through the material there tends to be a region in the diffraction spectrum at low energies where diffraction counts are unobservable. The extent to which the low-count region extends up the energy scale is determined by the density and thickness of the sample. This is an important consideration in the design of an EDXRD analyser since the major diffraction peaks must lie at energies that can easily penetrate through the sample. The diffraction peak energies are determined by the angle that the diffracted beam is measured, hence the diffraction angle must be chosen such that the peaks will lie at appropriate energies for the material being measured.

For a solid state detector like Cadmium Telluride the X-ray energy is absorbed by CdTe and then released directly as an electric signal. The electrical signal strength is directly proportional to the energy of the X-ray.

A centrally located opening (not shown) may be provided in each of the primary beam collimator 50 and scatter collimator 60 to enable alignment. In use a plug would block the respective openings.

Figure 2:
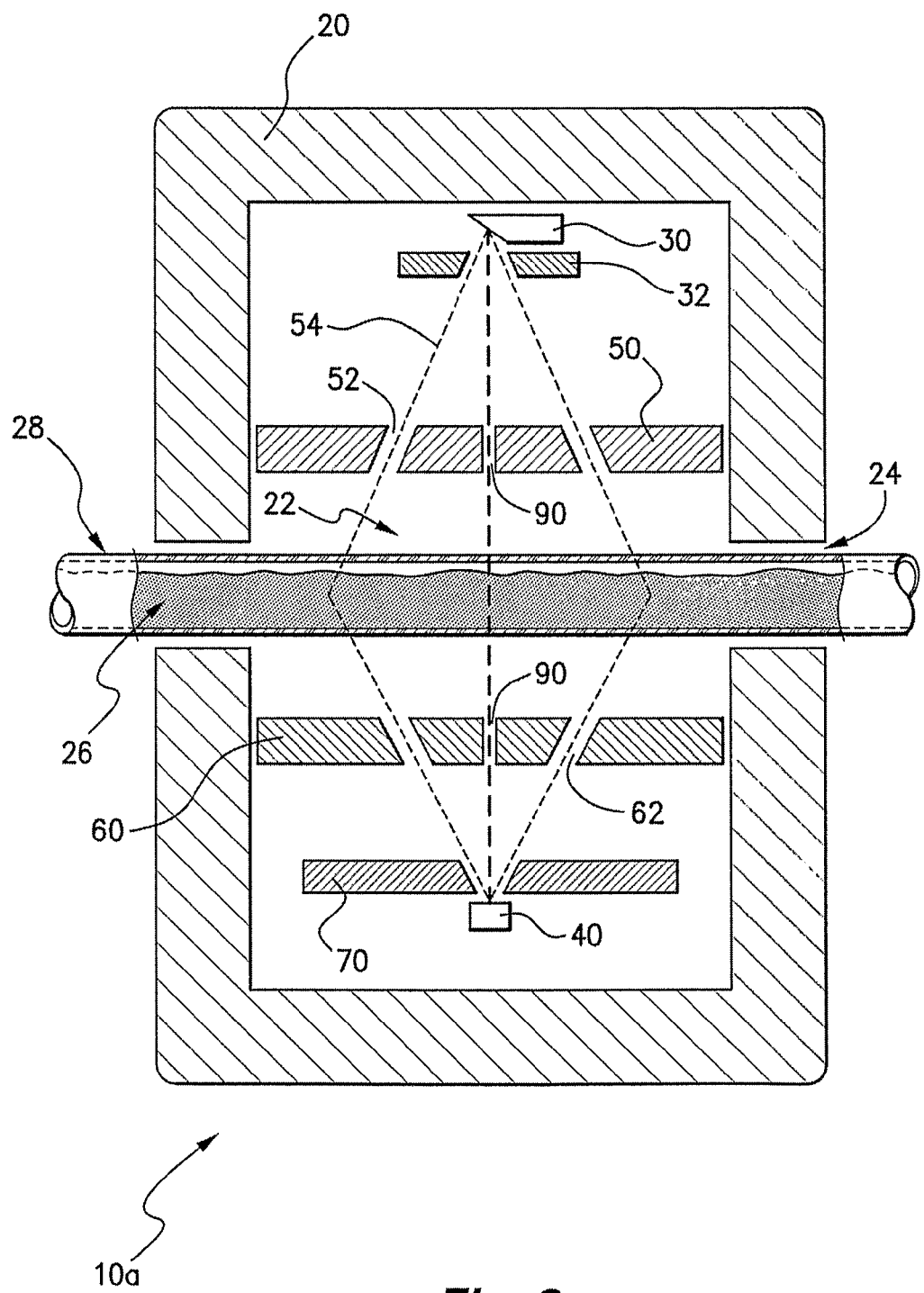
FIG. 2 is a schematic drawing of an alternative arrangement of an on-line EDXRD analyser for on-line mineralogical analysis.

FIG. 2 illustrates a further practical arrangement for installation of an on-line energy dispersive X-ray diffraction analyser 10a. However minor modifications have been made to the configuration of some of the components of the EDXRD analyser 10 as illustrated in FIG. 1. In particular, the primary beam collimator 50 and the scatter collimator 60 each include a cylindrical-shaped aperture 90 that penetrates through the entire thickness of the respective collimator plates 50, 60 and are aligned with each other along the central axis between the source 30 and the energy resolving detector 40. These cylindrical-shaped apertures 90 provide a means for the detector to measure a direct beam that is transmitted through the material in a process stream. Moreover, with reference to FIG. 1, detector 80 has been discarded and instead, detector 40 additionally measures the energy spectrum of directly transmitted X-rays. A mechanical means (not shown) allows the central apertures to be alternately opened and closed to allow the diffraction and transmission signals to be separately collected.

The diameter of the apertures 90 may be anywhere within the range of about a tenth of a millimeter to several millimeters. During diffraction measurements, the cylindrical-shaped apertures 90 of the primary beam collimator 50 and scatter collimator 60 are blocked by plugs (not shown) fabricated from tungsten. The thickness of the plugs is sufficient to completely stop the maximum X-ray energy used in the measurement. The central openings of the primary beam collimator 50 and scatter collimator 60 also provide a means for alignment.

The primary beam collimator 50 and scatter collimator 60 are manufactured from plates of metal and are designed in exactly the same manner. Previously referred to slits 52, 62, are produced by removing a conical section of the respective plate and replacing it with a conical piece of the same material having a smaller radius. This leaves an opening of constant width for a beam of X-rays to pass through.

Figure 3A:
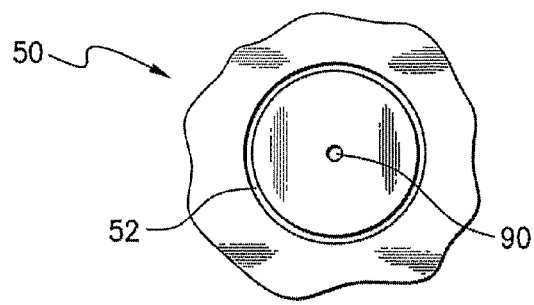
FIG. 3a is a schematic drawing of top view of the primary beam collimator illustrated in FIG. 2.
Figure 3B:
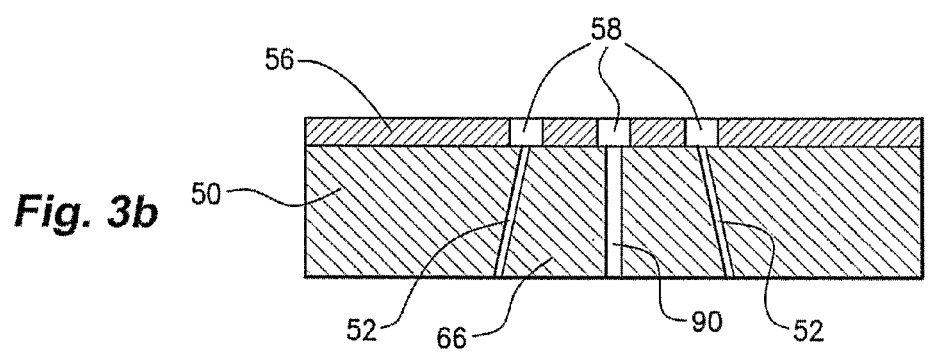
FIG. 3b is a schematic drawing of a side view of an alternate primary beam collimator.
Figure 3C:
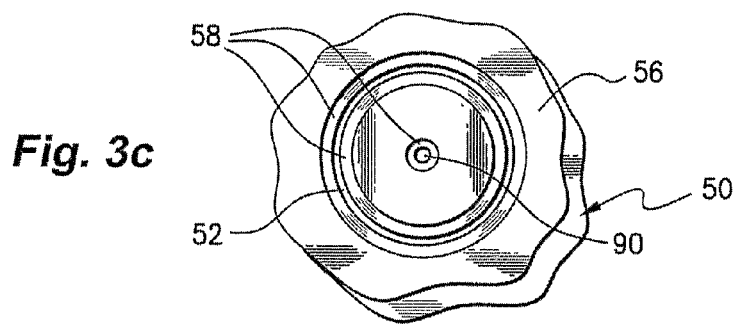
FIG. 3c is a schematic drawing of a top view of the primary beam collimator illustrated in FIG. 3b.

Referring to FIGS. 3a to 3c, and more particularly to FIG. 3b, it is evident that the inner surface of the slit 52 is sloped. This allows efficient passage of the beam of X-rays through the slit 52. The width of each slit 52, 62 may range from tenths of a millimeter to several millimeters. In the example illustrated in FIG. 1, the slit width of the primary beam and scatter collimators is the same. A wire cutting technique provides a highly accurate means of producing the slits 52, 62. A discontinuity (not shown) is provided in order that an inner conical section 64 is held in place relative to the collimator. However the discontinuity is kept as small as possible relative to the size and weight of the collimator since the larger the discontinuity, the smaller the total area of the aperture and hence the larger the reduction in count-rate.

The size, shape and thickness of the primary beam collimator 50 and scatter collimator 60 vary depending on the intended final application of the EDXRD analyser 10, or 10a. Manufacturing the primary beam collimator 50 and scatter collimator 60 from steel is advantageous as it is relatively low-cost compared to other metals and it can be machined precisely with relative ease.

Whilst not illustrated in FIG. 3a, an additional radiation shield 56, manufactured from lead, may be provided for each of the primary beam collimator 50 and scatter collimator 60 (see FIGS. 3b and 3c). The lead shield 56 covers the entire surface area of the side of each of the primary beam collimator 50 and scatter collimator 60 subjected to the X-ray beam, except for small cylindrical regions 58 around the slits 52, 62. The lead shield 56 is directly attached to its respective collimator and provides extra X-ray shielding on top of that provided by the steel section of the collimator. Lead is used in this case as the sheets do not need to be machined to a high accuracy as they are not used to collimate the X-ray beam.

The detector collimator 70 also includes a radiation shield (not shown) manufactured from lead. A cylindrical hole is removed from the detector collimator shield about the region of the conical aperture 72.

Figure 4:
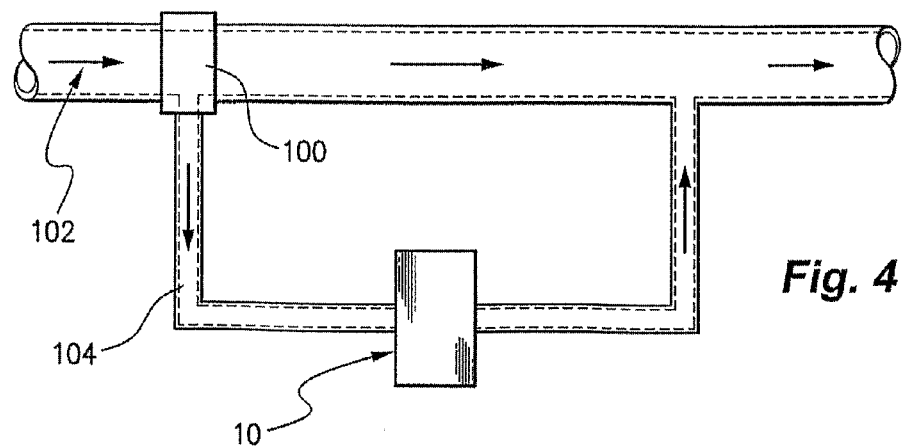
FIG. 4 is a schematic drawing of an alternative arrangement of an EDXRD analyser.

The components of the analyser described above are arranged such that the process stream of the industrial plant passes through the shielding 20. Alignment of the components requires careful precision. Configuring the analyser directly over the process stream is practical for applications where the diameter of the pipeline/conveyor is less than about 25 mm. However, the diameter of pipelines or conveyors within processing plants, generally, is considerably larger. In such circumstances a byline is provided, a schematic arrangement of which is illustrated in FIG. 4.

Sampler 100 diverts a representative portion of material from the process stream 102 into the byline 104. The material is then passed through the EDXRD analyser 10 or 10*a* (as described in relation to FIG. 1 or 2 above) and the material is then returned to the main process stream 102.

Figure 5A:
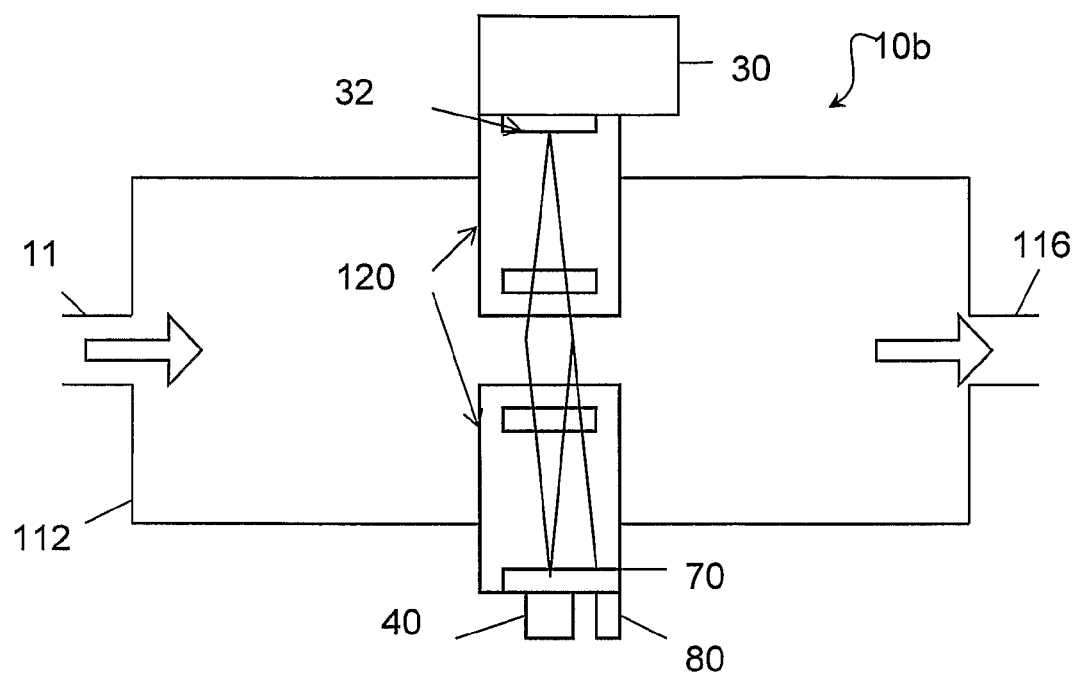
FIG. 5a is a schematic drawing of a top view of a further alternative arrangement of an on-line EDXRD analyser for on-line mineralogical analysis.
Figure 5B:
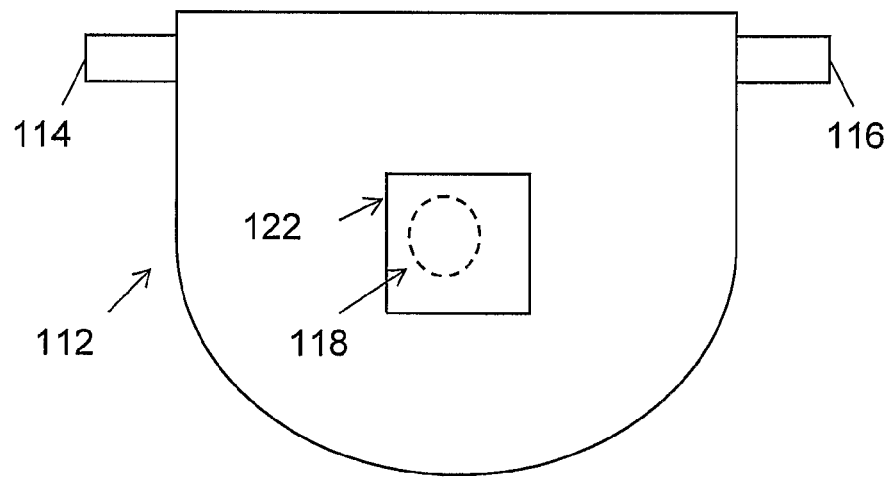

FIGS. 5*a* and 5*b* illustrate a still further practical arrangement for installation of an on-line energy dispersive X-ray diffraction analyser 10*b* which is particularly targeted to the mineralogical analysis of mineral slurries. The components of the EDXRD analyser 10*b* are the same as the components of the analyser illustrated in FIG. 1, with a few modifications which are now described. Unlike the arrangements previously described, in which material was passed through a pipe, here, the analyser 10*b* is submerged in a slurry tank 112. The slurry tank 112 (the housing) is provided and arranged with a slurry inlet 114 and slurry outlet 116. A feed from the process stream passes through the slurry tank via the slurry inlet 114 and the slurry outlet 116. In some applications, the pressure of the process stream may be sufficient to effect the transfer of material into the tank; alternatively, a pump or gravity feed may be used. The configuration and volume of the slurry tank 112 together with the pump characteristics rate ensure a constant flow of material in through the slurry inlet 114 and out of the slurry outlet 116, back into the process stream. The tank illustrated is suitable for flow rates up to about 60 liters per minute. Situated on either side of the slurry tank are beam access ports 118. In this embodiment, the primary beam collimator 50 and the scatter collimator 60 are rigidly fixed relative to the slurry tank 112. Each of the primary beam collimator 50 and the scatter collimator 60 are respectively mounted to a first end of a steel tube 120 which extends into the slurry tank 112. The second end of each of the steel tubes 120 is rigidly mounted to the respective beam access port 118. Certain portions of the first ends of the respective tubes may be joined to assist in maintaining precise alignment between the components of the analyser 10*b*. The X-ray source 30 and source collimator 32 are mounted to a first X/Y adjustable plate 122. Similarly the energy resolving X-ray detector 40, second detector 80 and detector collimator 70, are mounted to a second X/Y adjustable plate 122. Each plate is rigidly mounted to the tank 112.

The configuration of the X-ray diffraction analyser 10*b* illustrated in FIGS. 5*a* and 5*b* is advantageous in that a significantly higher volume of material may be analysed. Such a configuration may have significant benefits in terms of sampling accuracy and ease of maintenance.

As stated above, alignment of the component requires careful precision. The EDXRD analyser 10, 10*a*, 10*b* is particularly sensitive to misalignments of the polychromatic X-ray source 30, detector 40, source collimator 32, primary beam collimator 50, scatter collimator 60 and detector collimator 70 and any such misalignment will degrade both the count-rate and resolution of the instrument. The slits 52, 62 of the respective primary beam collimator and scatter collimator are circularly symmetric about a central axis between the source of X-rays 30 and the first X-ray detector 40. Symmetry offset from the central axis will increase the rate of error. Similarly, it is desired that the respective primary beam collimator and scatter collimator annular slits 52, 62 are as close to parallel to the direction of travel of the X-rays. Equally important is the alignment in the vertical direction of the primary beam collimator 50 and scatter collimator 60 with respect to the source 30 and detector 40, and in the horizontal direction of the primary beam collimator 50 and scatter collimator 60 with respect to the source 30 and detector 40.

Figure 6B:
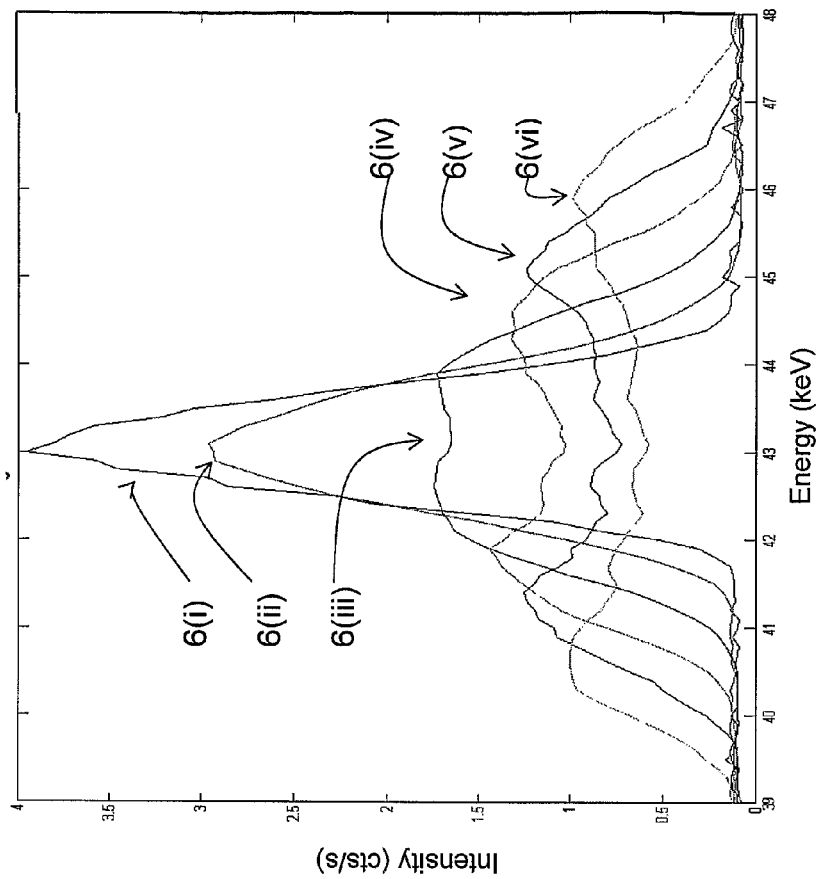
FIG. 6b is a graph illustrating the effect of misalignment shown in FIG. 6a on the diffraction peak.
Figure 6A:
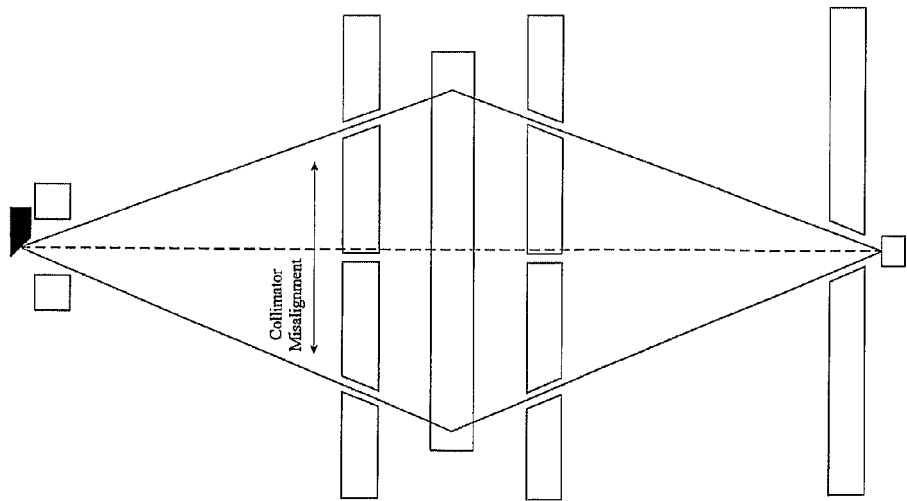
FIG. 6a is a schematic drawing of the EDXRD analyser of FIG. 2, subject to horizontal misalignment of the primary beam collimator and scatter collimator.

FIGS. 6*a* and 6*b* illustrate the effect of misalignment in the horizontal direction, of the primary beam collimator 50 and scatter collimator 60, on the resultant observed diffraction peaks. These results were obtained for an analyser where the primary beam collimator annular slit 52 and scatter collimator annular slit 62 each had a width of 0.5 mm and detector collimator aperture 72 a width of 1.2 mm. Referring to FIG. 6*b*, 6(*i*) refers to the plot where there is substantially no misalignment (0 mm), 6(*ii*) refers to the plot where there is a misalignment of 0.2 mm, 6(*iii*) refers to the plot where there is a misalignment of 0.4 mm, 6(*iv*) refers to the plot where there is a misalignment of 0.6 mm, 6(*v*) refers to the plot where there is a misalignment of 0.8 mm and 6(*vi*) refers to the plot where there is a misalignment of 1.0 mm. As can be seen, a misalignment of just 0.2 mm is enough to appreciably reduce the peak intensity and degrade the resolution (peak width.) However it will be appreciated that allowable misalignment will generally be larger for instruments with wider collimator openings.

Machining components so that the collimators are positioned with the required precision is difficult and expensive, considering that the collimators, source and detector are placed over a distance of several hundred millimeters but must be aligned within a few tenths of a millimeter.

Horizontal alignment is achieved by placing the primary beam collimator 50 and scatter collimator 60 on translation stages fitted with micrometers to allow for fine adjustment. The primary beam collimator 50 and scatter collimator 60 can be fixed together whilst holding acceptable tolerances since they are spaced reasonably close together (generally less than 100 mm.) This means that they may be aligned with a single adjustment. Alignment is achieved when the X-ray counts detected passing through the central openings are a maximum.

Figure 7B:
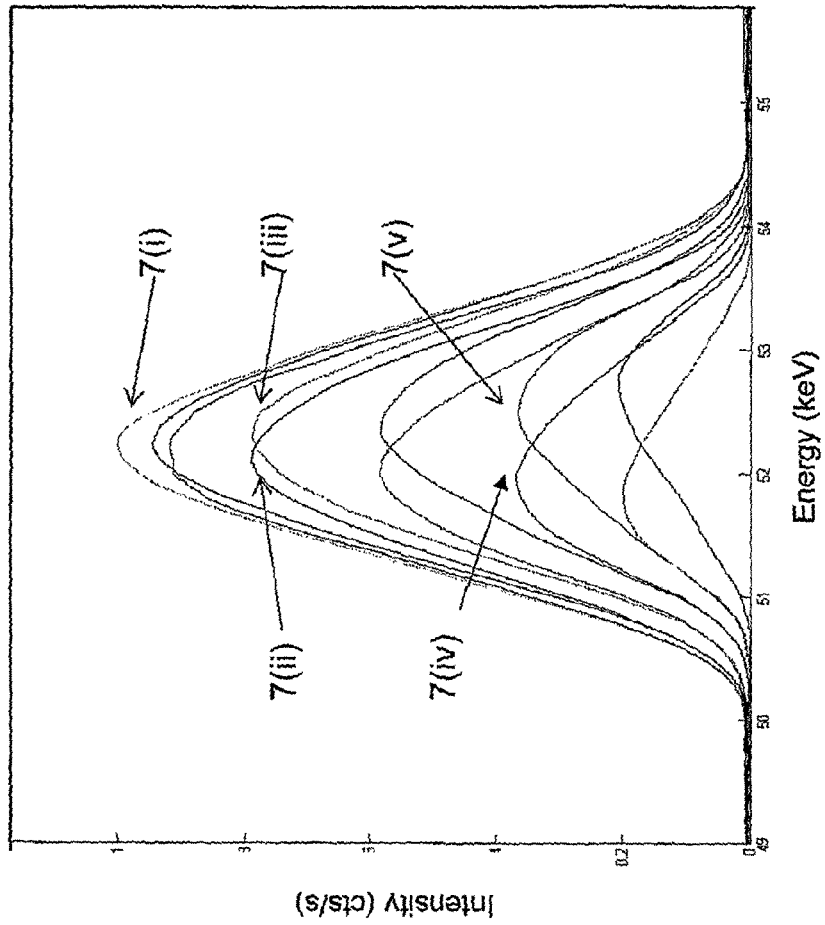
FIG. 7b is a graph illustrating the effect of misalignment shown in FIG. 6a on the diffraction peak.
Figure 7A:
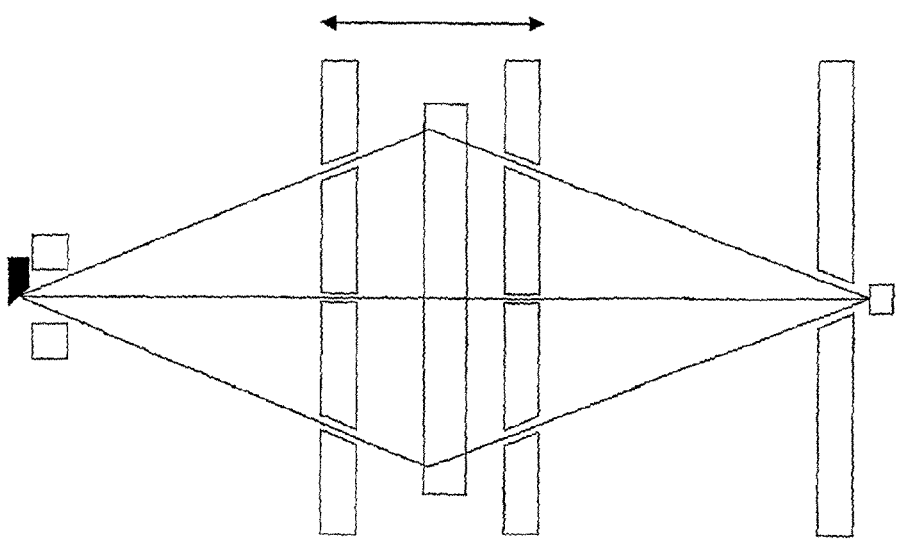
FIG. 7a is a schematic drawing of the EDXRD analyser of FIG. 2, subject to vertical misalignment of the primary beam collimator and scatter collimator.

Misalignment of the primary beam collimator annular slit 52 and scatter collimator annular slit 62 with respect to the source 30 and detector 40 in the vertical direction is less critical than in the horizontal. Referring to FIG. 7*b*, 7(*i*) refers to the plot where there is substantially no misalignment (0 mm), 7(*ii*) refers to the plot where there is a misalignment of +0.2 mm, 7(*iii*) refers to the plot where there is a misalignment of −0.2 mm, 7(*iv*) refers to the plot where there is a misalignment of +0.4 mm, 7(*v*) refers to the plot where there is a misalignment of −0.4 mm. It should be appreciated that the two plots between 7(*i*) and 7(*ii*), 7(*iii*) refers to those where the misalignment is ±0.1 mm, similarly those between 7(ii), 7(iii) and 7(iv) 7(v) refers to those where the misalignment is ±0.3 mm. As shown, misalignments of up to 2 mm are generally acceptable. The translation stages may be adjustable to fine tune alignment in the vertical direction however this is not as critical.

Figure 8:
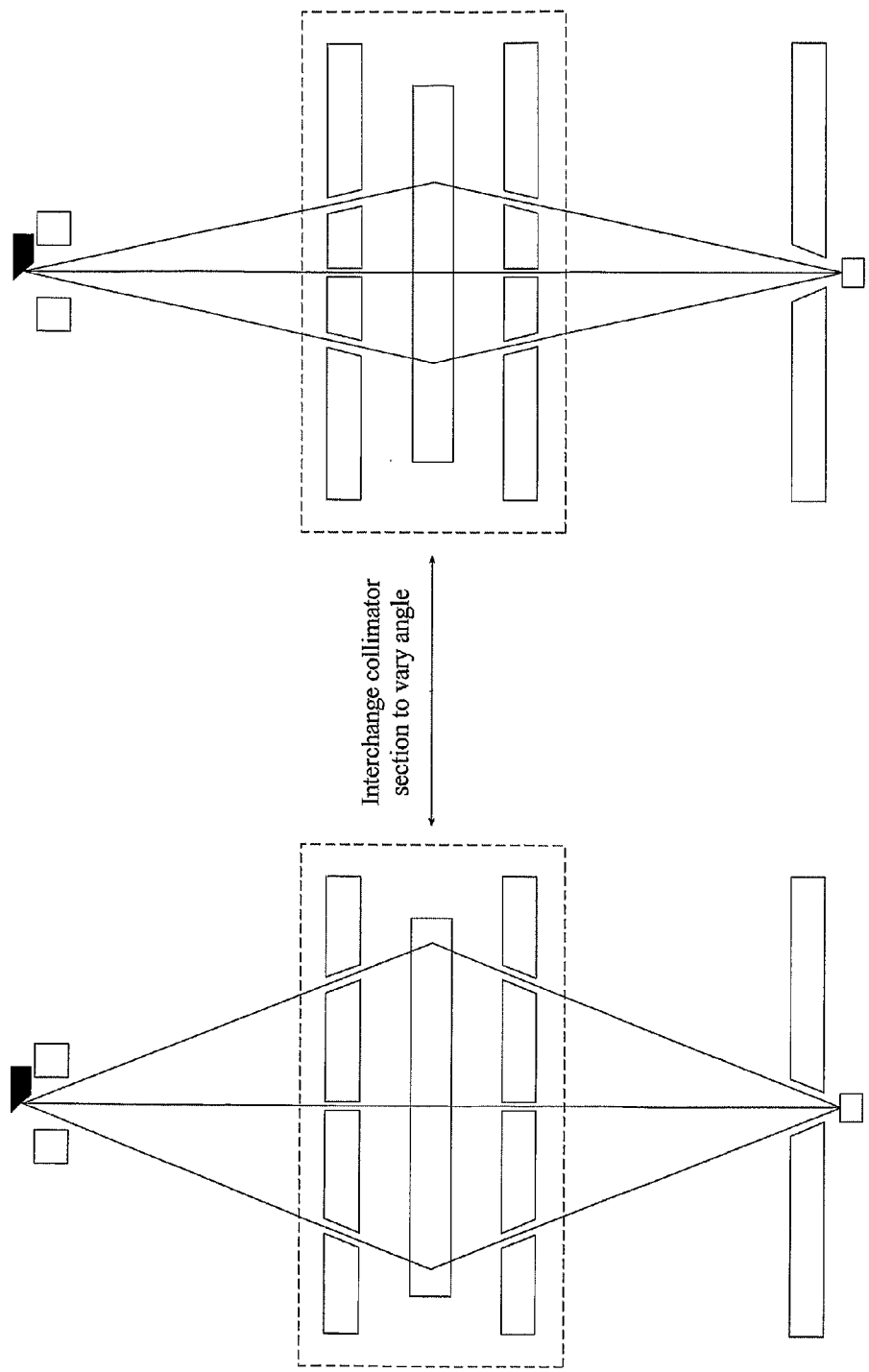
FIG. 8 is a schematic drawing showing the effect of interchanging components of the analyser effect a change in the diffraction angle.

Moreover, the EDXRD analyser 10, 10a, and preferably 10b, can be constructed to contain interchangeable components so that the parameters of the instrument, in particular the diffraction angle θ, can be varied easily to suit a particular application. The optimum arrangement of this is creating a system whereby an assembly, composed of the primary beam collimator 50 and scatter collimator 60, are removed and replaced with a different assembly, where the radius $r_1$ of annular slit 52 and the radius $r_2$ of annular slit 62 are varied. Such an arrangement is illustrated in FIG. 8.

Optionally the distance between the primary beam collimator 50 and scatter collimator 60 may be varied, with the respective slit aperture radius's remaining constant as with the distance between the source 30 and detector 40.

It is also possible that the analyser be configured, such that assemblies, on which the X-ray source 30 and detector(s) 40, (80) are mounted, are height-adjustable. This can be achieved using mounting plates that enable the source and detector collimator to be fixed at different distances from the sample. This feature is useful if it is desired to change the diffraction angle but the radius of the incident X-ray beam on the samples is required to be constant. This will often be the case since it is desirable to always have the beam width as wide as the sample itself so that the greatest possible amount of material is measured.

The main advantage of a modular design is the instrument can be altered to suit different applications, rather than having to use a different analyser. It also means that the analysers of different designs can be made of a set from standard components, reducing the cost of development and construction.

The processor (not shown) may normalise the measured spectrum by dividing the measured energy spectrum of the diffracted X-rays by the measured transmission of a direct beam of X-rays through the material. Normalization of the measured spectrum accounts for attenuation of the X-ray beam.

Considerable overlap may be present between the peaks of the different minerals. In order to resolve the presence of overlaps, the diffraction data may be processed using a simple linear regression technique. Accordingly, two or three energy 'windows' may be assigned to each mineral, placed around the clearest and most intense peaks for that mineral, and the total number of X-ray counts in each window determined for a particular period of time. Linear regression can be used to relate the window count-rates to mineral composition.

For situations where linear regression is not appropriate, deconvolution/regression may be appropriate. In such situations the spectrum is deconvoluted based on knowledge of the how the instrument and detector affect the profile of the diffraction spectrum. This can significantly decrease peak overlap. Regression analysis is then performed on the deconvoluted spectrum. Optionally, whole pattern analysis, for example, Rietveld analysis may be performed. In this situation the whole diffraction pattern is used to determine mineral quantities, not just the diffraction peaks as in linear regression. Whole pattern methods generally start with a calculated diffraction pattern and refinements are made to the variables used in the calculation until the calculated pattern matches the real spectrum as closely as possible. The mineral quantities are then determined from the refined variables. Whole pattern methods are preferred as they are generally more accurate than single peak methods.

Experimental Data and Analysis Results

Figure 9A:
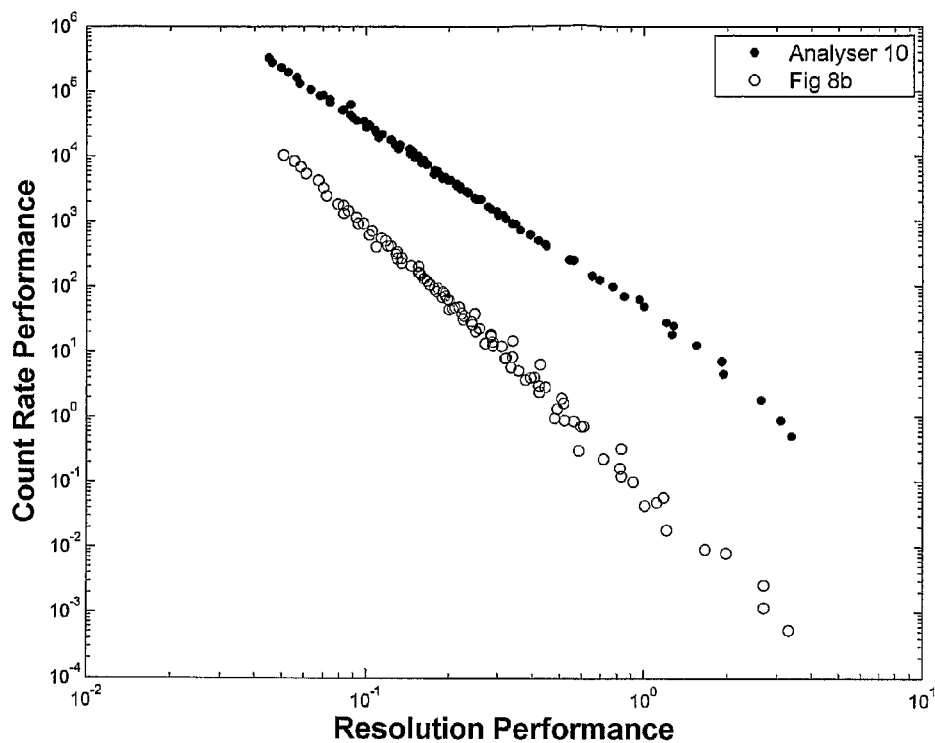
FIG. 9a is a graph showing the results of relative performance of the EDXRD analyser illustrated in FIG. 1 to an instrument referred to in the background art.
Figure 9B:
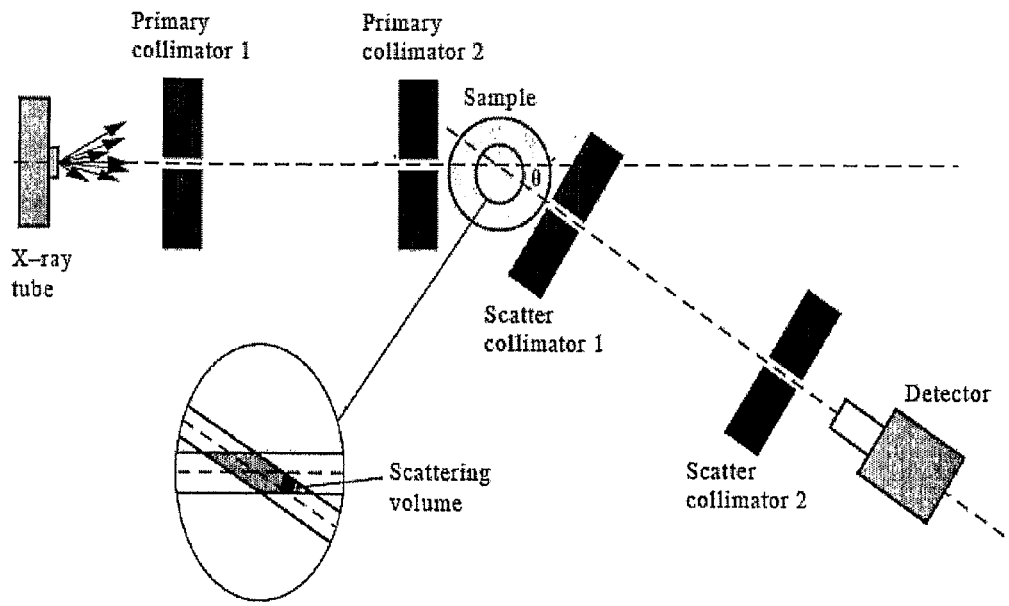

FIG. 9a shows simulation results of the relative performance of the EDXRD analyser 10 illustrated in FIG. 1, to a known instrument[6] schematically illustrated in FIG. 9b. Each data point represents a different configuration of the analyser 10 and instrument, where the variation was due to collimator opening widths (which were varied between 0.1 mm and 2.0 mm) and source-to-sample and sample-to-detector distances. As the results are simulated, the diameter of the primary beam collimators and detector collimator apertures, and alignment between components of the known instrument are assumed to be precise, and consistent with that of the analyser 10.

Despite this precision, it is readily observable that the performance of the analyser 10 in accordance with the invention is far superior to the known instrument illustrated in FIG. 9b, where the count-rate performance at any value of resolution is more than an order of magnitude larger for the analyser 10 in accordance with the invention.

Advantageously, the EDXRD analyser 10 in accordance with the invention enables a much larger volume of material to be measured than the instrument illustrated in FIG. 9b. In the instrument of FIG. 9b, the incident beam has a very small diameter, generally less than 2 mm and hence only a small volume of material is measured, whereas the analyser 10 in accordance with the invention measures a ring of material with a diameter in the tens of millimeters. This is a significant advantage as sampling errors are reduced and a more representative assessment of the material composition given.

Figure 10A:
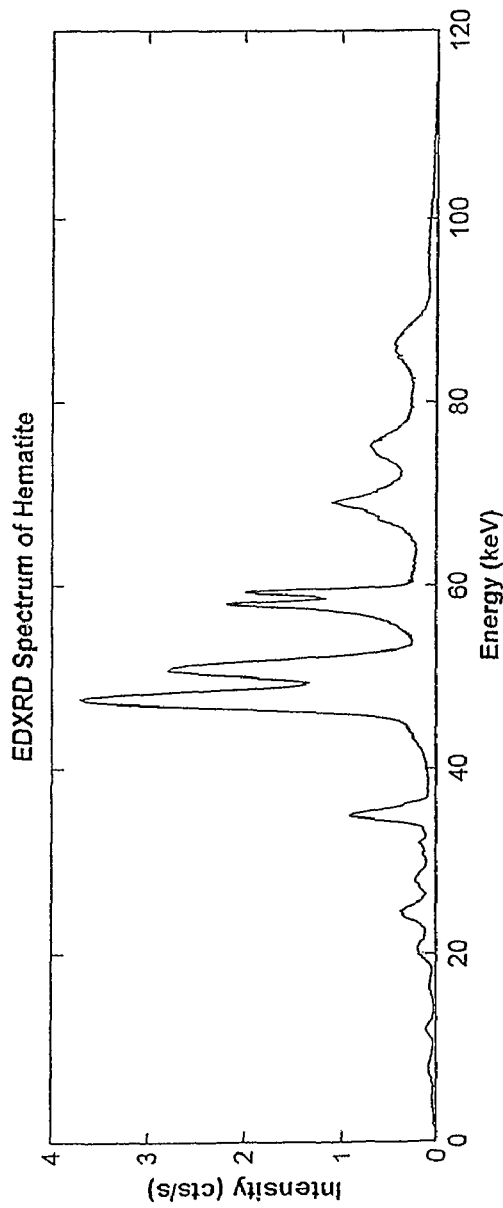
FIGS. 10a and 10b are graphs of EDXRD spectrum of single minerals rutile and hematite respectively, acquired from the analyser in accordance with the invention.
Figure 10B:
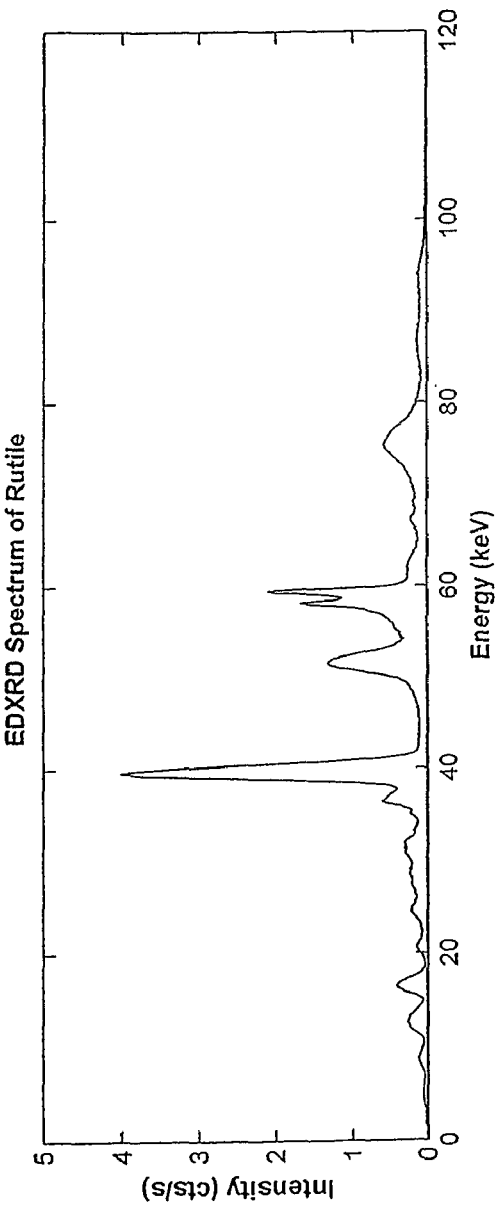

Shown in FIGS. 10a and 10b are example EDXRD spectra of the minerals hematite ($Fe_2O_3$) (FIG. 10a) and rutile ($Ti_2O$) (FIG. 10b) acquired with the apparatus 10. The spectra were collected with an X-ray tube potential of 120 kV and current of 0.5 mA. The diffraction spectra contain sets of diffraction peaks that represent reflections from different crystal planes.

Figure 11:
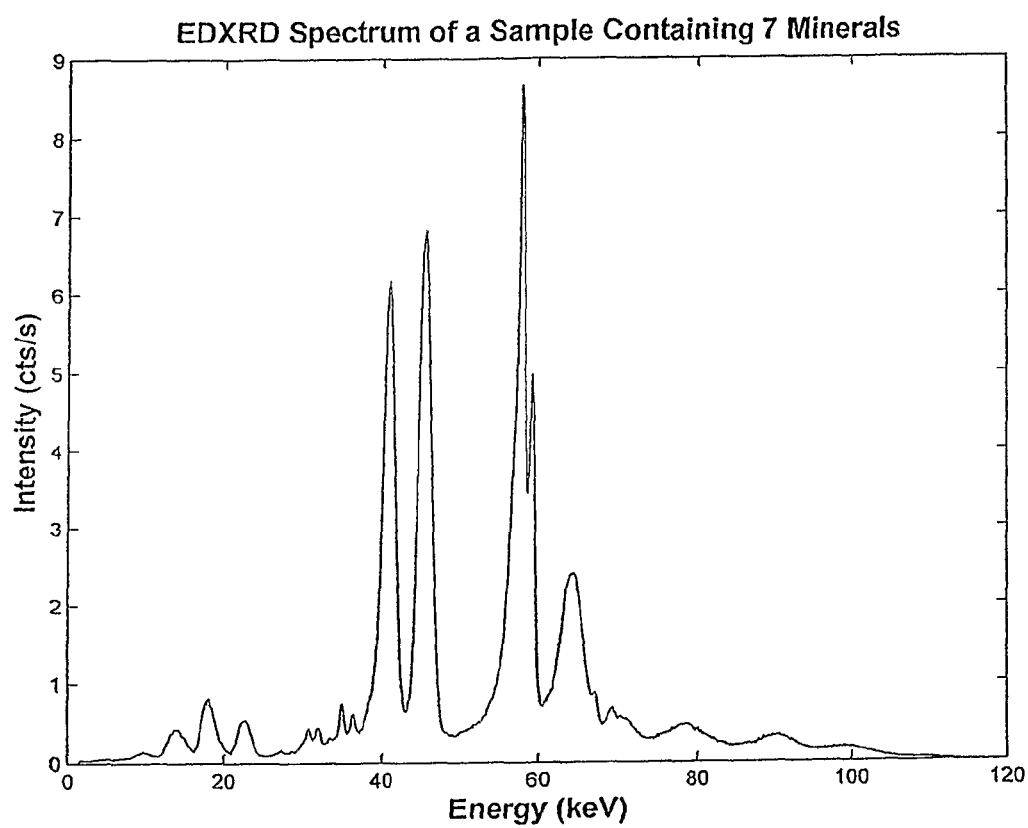
FIG. 11 is a graph of EDXRD spectrum of a mixture of minerals acquired with the apparatus illustrated in FIG. 1.

Shown in FIG. 11 is an example of an EDXRD spectrum, acquired with the apparatus 10, for a sample containing halite (NaCl) and sylvite (KCl) as the major components in quantities of approximately 50 wt % and 40 wt % respectively, and hematite ($Fe_2O_3$), quartz ($SiO_2$), gypsum ($CaSO_4.2(H_2O)$), anhydrite ($CaSO_4$) and kaolinite ($Al_2Si_2O_5(OH)_4$) as the minor components (all <5 wt %). The four strong peaks between 35 keV and 70 keV belong to the major components, halite and sylvite. Fifteen such samples were made, each containing a slightly different amount of each mineral. The accuracy with which each of the seven minerals can be quantified was determined by analysing the spectra of the fifteen samples. Unlike widely used on-line elemental analysis techniques for process monitoring and control, it was found that the major components can be quantified with an accuracy of less than 0.5 wt % and the minor components with an accuracy of approximately 0.2 wt %.

As will be evident from the foregoing examples, the EDXRD analyser in accordance with the invention uses transmission techniques compared to reflection techniques utilised by many conventional analysers. Comparatively an EDXRD analyser in accordance with the invention enables much higher X-ray energies (for example, 120 keV for an EDXRD analyser compared with about 10 keV for a typical conventional analyser). The advantage of this is that greater thicknesses of materials can be measured reliably. An EDXRD analyser in accordance with the invention is easily capable of measuring material tens of millimeters in thickness. Moreover the use of higher energy X-rays in EDXRD reduces the effect of micro-absorption which significantly reduces the need for sample preparation.

A further advantage of an EDXRD analyser in accordance with at least one embodiment of the invention is that there are no moving parts. Lack of moving parts reduces complexity and cost of the analyser due to mechanical wear and tear.

Whilst the above embodiments have been described in relation to the pumping of a mineral, certain embodiments are applicable for use with gravity fed slurries, pneumatically fed dry powders, screw fed dry powders and conveyed materials. With regard to gravity fed slurries the process stream is fed through the analyser under the influence of gravity. In this arrangement the pipeline 28 illustrated in FIGS. 1 and 2, is in a vertical orientation. The relative configuration of the components of the analyser remains the same. The pipeline may be either the main process stream or a by-line. The pipeline will most likely be manufactured from a low density material having a low atomic number. When the material under consideration is a dry power, a pneumatic system may used to blow the material through the analyser, via a pipeline. With regard to screw fed dry powders the material may be forced through the analyser via a turning screw. Material may optionally be conveyed through the analyser. However due to the risk of material build up inside the analyser this is the least preferred option.

In the above described examples, the aperture widths of the primary beam collimator 50 and scatter collimator 60 are the same, however in some cases in may be deemed more advantageous to use a different opening width for each collimator 50, 60. Whilst the primary beam collimator 50 and scatter collimator 60 have been described as being machined from steel, it should be appreciated that other materials could be used. For example, possible materials that could be used include lead and tungsten, however these materials are less favourable to steel as they suffer from the disadvantage that they are difficult to machine precisely. Tungsten has a further disadvantage in that it is also expensive compared to steel.

In the above described examples, the source collimator 26 has a conical-shaped aperture at its centre. In an optional embodiment the source collimator has a cylindrical-shaped aperture at its centre.

In the above described examples, X-rays were produced using a Hamamatsu L8121-01 Microfocus X-ray tube, operated at a voltage of 120 kV and a current of 0.5 mA. However within an industrial environment it is envisaged that the X-ray source will be a higher power X-ray tube than the Hamamatsu tube used in the test rig. It will mostly likely be operated between 70-120 kV and several mAs.

In the above described examples the EDXRD analyser uses a CdTe detector. The size of the CdTe crystals in this detector is quite small, in the case of the XR-100T-CdTe detector used in the test rig the detector size is 3×3×1 mm$^3$, so clearly the measured beam must have a very small diameter at the point of detection. The analyser 10 in accordance with the invention satisfies this requirement because the diffracted beam is measured at the apex of a converging cone. Furthermore, CdTe detectors are able to be operated a room temperature.

Whilst less desirable, other possible X-ray detectors include high-purity germanium (HPGe). In an embodiment incorporating an HPGe detector it will be appreciated that a cooling system will be necessary.

It should be appreciated that the term translation stage, generally describes a component of a motion system which is used to restrict an object to one or more axis of motion. A translation stage typically has a platform and a base, joined by some form of guide or linear bearing in such a way that the platform is restricted to motion with respect to the base in the X and Y directions. In common usage, the term translation stage may or may not also include the mechanism by which the position of the platform is controlled relative to the base.

The analyser 10 is suitable for monitoring a large number of mineralogical processes. Non-limited example applications include iron ore, bauxite, copper ore, nickel ore, Portland cement and other applications involving the processing of minerals. As will be appreciated, the diffraction angle will vary depending on the application and thus the optimum geometric configuration will be decided.

For applications where a continuous flow of material is measured, the volume of material passing through the analyser 10 may vary from a few litres per minute up to hundreds of lire per minute.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Sutherland, D. N., Gottlieb, P., 1991 "Application of Automated Quantitative Mineralogy in Mineral Processing, Miner. Eng., 4, pp 753-762.
2. Roach, G., 1998. "Application of Emerging Analytical Technologies to the Bayer Process, technology—Australia's Further: New Technology for Traditional Industry: Proceedings of the 1998 Invitational Symposium, Fremantle, Australia.
3. Smallbone, A. H., 1997. "Automated On-line Analysis for Controlling Industrial Processes, Pure Appl. Chem., 49, pp 1609-1620.
4. Lim, C. S., Sowerby, B. D., 2005 "On-line Bulk Elemental Analysis in the Resource Industries Using Neutron-Gamma Techniques, J. Radioanal. Nucl. Chem., 264, (1) pp 15-19.
5. Scarlett, N. V. Y., Madsen, I. C., Manais, C., Retallack, D., 2001. "On-line X-ray Diffraction for Quantitative Phases Analysis: Application in the Portland Cement Industry, Power diffraction 16(2), pp 71-80.
6. Farquharson M. J and Speller R. D, 1998 "Trabecular bone mineral density measurements using EDXRD", J. Radiat Phys. Chem. Vol, 51 No 4-6, pp 607-608.

The invention claimed is:

1. An on-line energy dispersive x-ray diffraction (EDXRD) analyser for mineralogical analysis of material in a process stream, the EDXRD analyser comprising:
    a housing defining an analysis zone and having a passageway through it to allow transport of material in a process stream to pass through the analysis zone;
    a collimated source of polychromatic X-rays and an energy resolving X-ray detector, each of which are disposed in relation to the housing;
    a primary beam collimator disposed between the collimated source of polychromatic X-rays and the energy resolving X-ray detector, the primary beam collimator comprising an annular conical slit which defines a diverging incident beam of polychromatic X-rays to irradiate a portion of the analysis zone;
    a scatter collimator disposed between the primary beam collimator and the energy resolving X-ray detector, the scatter collimator comprising an annular conical slit which defines a diffracted beam of X-rays scattered by the material to converge towards the energy resolving X-ray detector; and
    a detector collimator comprising a conical opening which further defines the diffracted beam of X-rays scattered by the material;

where the energy resolving X-ray detector measures an energy spectrum of the diffracted X-rays at a predetermined diffraction angle, where the relative positioning of each of the source of polychromatic X-rays, the primary beam collimator, the scatter collimator, the energy resolving X-ray detector and detector collimator defines the diffraction angle, and where at least one of the primary beam collimator and the scatter collimator further comprises an aperture, the or each aperture arranged to enable a detector to measure the transmission of a direct beam of X-rays through the material.

2. An EDXRD analyser according to claim 1, where each of the primary beam collimator and the scatter collimator have an aperture, the respective apertures aligned with each other along a central axis between the collimated source of polychromatic X-rays and the energy resolving X-ray detector.

3. An EDXRD analyser according to claim 1, further comprising a second detector separate from the energy resolving detector.

4. An EDXRD analyser according to claim 3, where the scatter collimator includes an aperture aligned with respect to a segment of the annular conical slit of the primary beam collimator to enable the transmission of a direct beam of X-rays to impinge upon the second detector.

5. An EDXRD analyser according to claim 1, further comprising a signal processor to process signals from the detector(s) so as to determine planar spacings of minerals within the process stream.

6. An EDXRD analyser according to claim 1, where the slits of the respective primary beam collimator and scatter collimator are circularly symmetric about a central axis between the collimated source of polychromatic X-rays and the energy resolving X-ray detector.

7. An EDXRD analyser according to claim 6, where the width of the respective annular conical slits of the primary beam collimator and scatter collimator are within the range of 0.1 mm and 2.0 mm.

8. An EDXRD analyser according to claim 1, where the slits of the respective primary beam collimator and scatter collimator are discontinuous.

9. An EDXRD analyser according to claim 1, where the incident beam of X-rays which irradiates the portion of the analysis zone is in the form of a surface of a divergent hollow cone.

10. An EDXRD analyser according to claim 9, where the diffracted beam of X-rays scattered by the material is in the form of a surface of a convergent hollow cone.

11. An EDXRD analyser according to claim 1, where the source of polychromatic X-rays is a sealed X-ray tube.

12. An EDXRD analyser according to claim 1, where the source of X-ray is operable at a voltage between 80 kV and 120 kV.

13. An EDXRD analyser according to claim 1, where the energy resolving X-ray detector is a CdTe detector or another high-resolution semiconductor that is operable substantially at room temperature.

14. An EDXRD analyser according to claim 1, where the energy resolving X-ray detector is an HPGe detector.

15. An EDXRD analyser according to claim 14, further comprising a cooling system to cool the HPGe detector to a temperature sufficient to measure spectral data.

16. An EDXRD analyser according to claim 1, further comprising a source collimator in close proximity to, or attached to the source of X-rays, where the source collimator has one of a cylindrical-shaped aperture, and a conical-shaped aperture.

17. An EDXRD analyser according to claim 1, further comprising a first translation stage upon which is mounted the primary beam collimator and a second separate translation stage upon which is mounted the scatter collimator.

18. An EDXRD analyser according to claim 1, where the primary beam collimator and the scatter collimator are rigidly fixed relative to the housing, the EDXRD analyser further comprising a first translation stage upon which is mounted the X-ray source and source collimator and a second translation stage upon which is mounted the energy resolving X-ray detector and detector collimator.

19. An EDXRD analyser according to claim 18, where at least a portion of the housing comprises a vessel having an inlet and an outlet and through which material in a process stream passes.

* * * * *